(12) United States Patent
Addison

(10) Patent No.: US 9,078,609 B2
(45) Date of Patent: Jul. 14, 2015

(54) EXTRACTION OF PHYSIOLOGICAL MEASUREMENTS FROM A PHOTOPLETHYSMOGRAPH (PPG) SIGNAL

(75) Inventor: Paul Stanley Addison, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 1417 days.

(21) Appl. No.: 12/244,141

(22) Filed: Oct. 2, 2008

(65) Prior Publication Data
US 2010/0087720 A1    Apr. 8, 2010

(51) Int. Cl.
| A61B 5/05 | (2006.01) |
| A61B 5/00 | (2006.01) |
| A61B 5/1455 | (2006.01) |
| A61B 5/0205 | (2006.01) |
| A61B 5/021 | (2006.01) |
| A61B 5/024 | (2006.01) |

(52) U.S. Cl.
CPC ............. *A61B 5/14551* (2013.01); *A61B 5/021* (2013.01); *A61B 5/024* (2013.01); *A61B 5/0205* (2013.01); *A61B 5/7239* (2013.01)

(58) Field of Classification Search
CPC ............... A61B 5/7235–5/7267; A61B 5/7225
USPC ........................... 600/322, 323, 330, 331, 336
See application file for complete search history.

(56) References Cited

U.S. PATENT DOCUMENTS

| 3,835,840 A | 9/1974 | Mount |
| 4,561,447 A | 12/1985 | Kawamura et al. |
| 4,729,382 A | 3/1988 | Schaffer |
| 4,928,700 A | 5/1990 | Harada |
| 4,934,372 A | 6/1990 | Corenman et al. |
| 4,951,679 A | 8/1990 | Harada |
| 4,976,268 A | 12/1990 | Kurosawa et al. |
| 5,103,831 A | 4/1992 | Niwa |
| 5,131,400 A | 7/1992 | Harada |
| 5,170,796 A | 12/1992 | Kobayashi |
| 5,238,000 A | 8/1993 | Niwa |
| 5,241,964 A | 9/1993 | McQuilkin |
| 5,255,686 A | 10/1993 | Takeda et al. |

(Continued)

OTHER PUBLICATIONS

Geddes, LA, Handbook of Blood Pressure Measurement, Clifton, New Jersey, Humana Press, 1991.

(Continued)

*Primary Examiner* — Brian Szmal
*Assistant Examiner* — H. Q. Nguyen
(74) *Attorney, Agent, or Firm* — Shvarts & Leiz LLP

(57) ABSTRACT

The present disclosure relates to signal processing and, more particularly, to determining the value of a physiological parameter, such as the blood oxygen saturation ($SpO_2$) of a subject. In an embodiment, a first baseline for a first waveform and a second baseline for a second waveform are determined. In this embodiment, the first and second waveforms are indicative of the physiological parameter of the subject. The first and second waveforms are filtered to obtain a first direct-current (DC) component for the first waveform and a second DC component for the second waveform. A measured value for the physiological parameter is derived from the first and second baseline signals, and the first and second DC components. In an embodiment, the measured value for the physiological parameter is determined based on a ratio of the normalized difference between the DC component and the baseline signal for the first waveform with respect to same for the second waveform.

12 Claims, 6 Drawing Sheets

(56) References Cited

U.S. PATENT DOCUMENTS

| | | | |
|---|---|---|---|
| 5,351,685 A * | 10/1994 | Potratz | 600/330 |
| 5,431,159 A | 7/1995 | Baker | |
| 5,438,983 A | 8/1995 | Falcone | |
| 5,450,852 A | 9/1995 | Archibald et al. | |
| 5,467,771 A | 11/1995 | Narimatsu | |
| 5,490,506 A | 2/1996 | Takatani | |
| 5,497,779 A | 3/1996 | Takaya | |
| 5,503,148 A | 4/1996 | Pologe | |
| 5,564,427 A | 10/1996 | Aso et al. | |
| 5,575,284 A | 11/1996 | Athan | |
| 5,617,868 A | 4/1997 | Harada | |
| 5,676,140 A | 10/1997 | Ukawa | |
| 5,709,212 A | 1/1998 | Sugo | |
| 5,720,292 A | 2/1998 | Poliac | |
| 5,738,103 A | 4/1998 | Poliac | |
| 5,755,669 A | 5/1998 | Ono et al. | |
| 5,776,071 A | 7/1998 | Inukai | |
| 6,002,952 A | 12/1999 | Diab | |
| 6,027,453 A | 2/2000 | Miwa | |
| 6,027,455 A | 2/2000 | Inukai et al. | |
| 6,067,462 A | 5/2000 | Diab | |
| 6,157,850 A | 12/2000 | Diab et al. | |
| 6,263,222 B1 | 7/2001 | Diab et al. | |
| 6,516,209 B2 * | 2/2003 | Cheng et al. | 600/323 |
| 6,553,242 B1 * | 4/2003 | Sarussi | 600/330 |
| 6,658,277 B2 | 12/2003 | Wasserman | |
| RE38,476 E | 3/2004 | Diab et al. | |
| 6,699,194 B1 | 3/2004 | Diab | |
| 6,773,397 B2 | 8/2004 | Kelly | |
| 6,783,498 B2 | 8/2004 | Sackner | |
| 6,822,564 B2 | 11/2004 | Al-Ali | |
| 6,826,419 B2 | 11/2004 | Diab | |
| 7,184,809 B1 | 2/2007 | Sterling | |
| 7,215,984 B2 | 5/2007 | Diab et al. | |
| 7,215,986 B2 | 5/2007 | Diab et al. | |
| 7,257,433 B2 | 8/2007 | Takamura et al. | |
| 2003/0114737 A1 | 6/2003 | Nagai et al. | |
| 2005/0187448 A1 | 8/2005 | Petersen et al. | |
| 2006/0258921 A1 | 11/2006 | Addison | |
| 2007/0066910 A1 | 3/2007 | Inukai et al. | |
| 2007/0149872 A1 | 6/2007 | Zhang et al. | |
| 2007/0225582 A1 | 9/2007 | Diab et al. | |
| 2008/0208019 A1 | 8/2008 | Nitzan | |
| 2008/0214903 A1 | 9/2008 | Orbach | |
| 2008/0214942 A1 | 9/2008 | Oh et al. | |
| 2008/0287788 A1 * | 11/2008 | Richardson et al. | 600/437 |
| 2009/0048497 A1 | 2/2009 | Keren | |

OTHER PUBLICATIONS

Moyle, John TB, Hahn, CEW, Adams, Anthony P, Pulse Oximetry, Revised Edition, London, BMJ, 1998.

PCT International Search Report, International application No. PCT/IB2009/006897, International filing date: Sep. 17, 2009, Priority Date: Oct. 2, 2008, Applicant: Nellcor Puritan Bennett Ireland.

\* cited by examiner

EXTRACTION OF PHYSIOLOGICAL MEASUREMENTS FROM A PHOTOPLETHYSMOGRAPH (PPG) SIGNAL

SUMMARY

The present disclosure relates to signal processing and, more particularly, to determining the value of a physiological parameter, such as the blood oxygen saturation ($SpO_2$) of a subject, from a signal, such as a photoplethysmograph (PPG) signal.

In an embodiment for determining the $SpO_2$ of a subject, a red light signal (R) and an infrared light signal (IR) indicative of the blood oxygen saturation of a subject under examination are received. A respective baseline may be determined for each of the red light and the infrared light signals. In an embodiment, the baseline for each signal may be determined, at least in part by computing a curve that passes through the troughs of the pulses carried in the signal. In this embodiment, the pulsatile information may be advantageously ignored in estimating the baseline, thereby minimizing errors from fluctuations in the pulse. In an embodiment, the baseline for each signal may be determined, at least in part, by computing a curve that passes through the peaks of the pulses carried in the signal. The received red and infrared signals are also filtered to obtain direct-current (DC) components $D_R$ and $D_{IR}$ for the red light and infrared light signals, respectively. Difference signals $A_R$ and $A_{IR}$ are determined for the red light and the infrared light signals, respectively. In an embodiment, the difference signal for a signal corresponds to the difference between the amplitude of the baseline signal and the amplitude of direct-current component. The difference signals are normalized to obtain normalized difference signals $A^*_R$ and $A^*_{IR}$ for the red light and the infrared light signals, respectively. In an embodiment, the difference signals are normalized by dividing the amplitude of the difference signal by the respective DC offset. Other normalizations, including dividing by the baseline signal, may also be used. A measured value for the physiological parameter may be derived from a ratio $\alpha$ of the normalized difference signal $A^*_R$ with respect to the normalized difference signal $A^*_{IR}$. In an embodiment, the measured value for the physiological parameter may be derived by feeding the ratio $\alpha$ to a lookup table. Other suitable algorithms for determining a measured value of the physiological parameter from the ratio may be used. The measured physiological parameter may be used in any suitable known and/or yet to be known medical applications, such as, for example, to monitor a patient's health status. In an embodiment, the measured physiological parameter may be used to trigger an alarm when specified conditions (e.g., a predetermined threshold) are met.

A method or system of measuring physiological parameters based on the afore-mentioned embodiments may advantageously minimize reliance on the pulsatile part of the waveform. Therefore, erroneous information within the waveform, or certain changes in the structure of the pulse wave (e.g., the position of the dichrotic notch) have minimal if any adverse impact on the predictive value of the physiological parameter.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
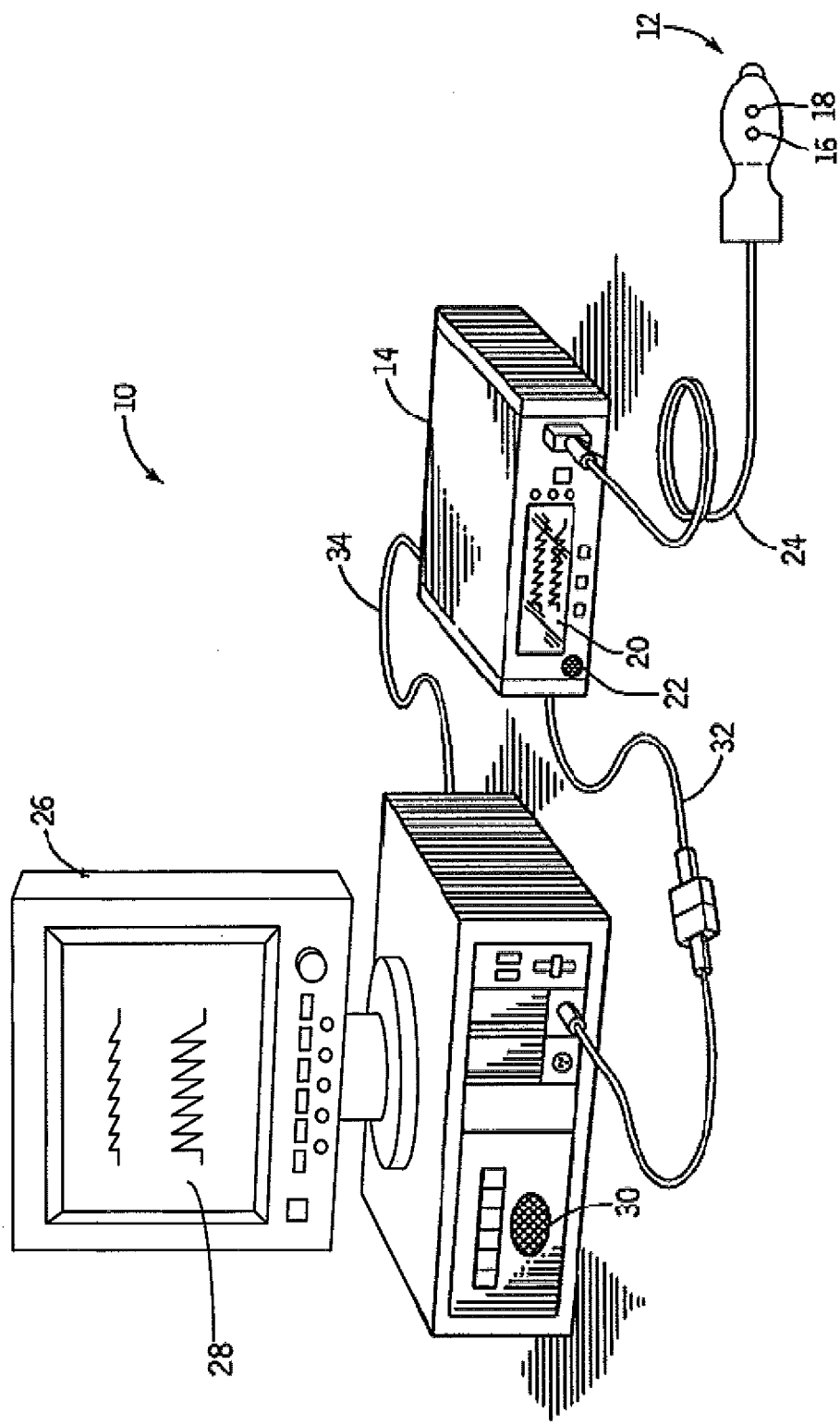
FIG. 1 shows an illustrative pulse oximetry system in accordance with an embodiment.

An oximeter is an instrument that may determine the oxygen saturation of the blood. One common type of oximeter is a pulse oximeter, which determines oxygen saturation by analysis of an optically sensed plethysmograph.

A pulse oximeter is a medical device that may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambelt-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
λ=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda,t)}{dt} \simeq \log I(\lambda, t_2) - \log I(\lambda, t_1)$$

Using log A-log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPO maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t)=[I(t_2,\lambda_{IR})-I(t_1,\lambda_{IR})]I(t_1,\lambda_R)$$

$$y(t)=[I(t_2,\lambda_R)-I(t_1,\lambda_R)]I(t_1,\lambda_{IR})$$

$$y(t)=Rx(t) \quad (8)$$

FIG. 1 shows an illustrative pulse oximetry system 10 in accordance with an embodiment. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to an embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data, whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Pulse oximetry monitor 14 may be configured to calculate physiological parameters based at least in part on data received from sensor 12 relating to light emission and detection. For example, in an embodiment, pulse oximetry monitor 14 may include signal processing system 480 (described below with reference to FIG. 4c) and may generate a measured value for the physiological parameter using process 450 (described below with reference to FIGS. 4a and 4b). In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood oxygen saturation generated by pulse oximetry monitor 14 (referred to as an "SpO$_2$" measurement), pulse rate information from monitor 14, and blood pressure from a blood pressure monitor (not shown) on display 28. In an embodiment, multi-parameter patient monitor 26 may include signal processing system 480 (described below with reference to FIG. 4c) and may generate a measured value for the physiological parameter using process 450 (described below with reference to FIGS. 4a and 4b).

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
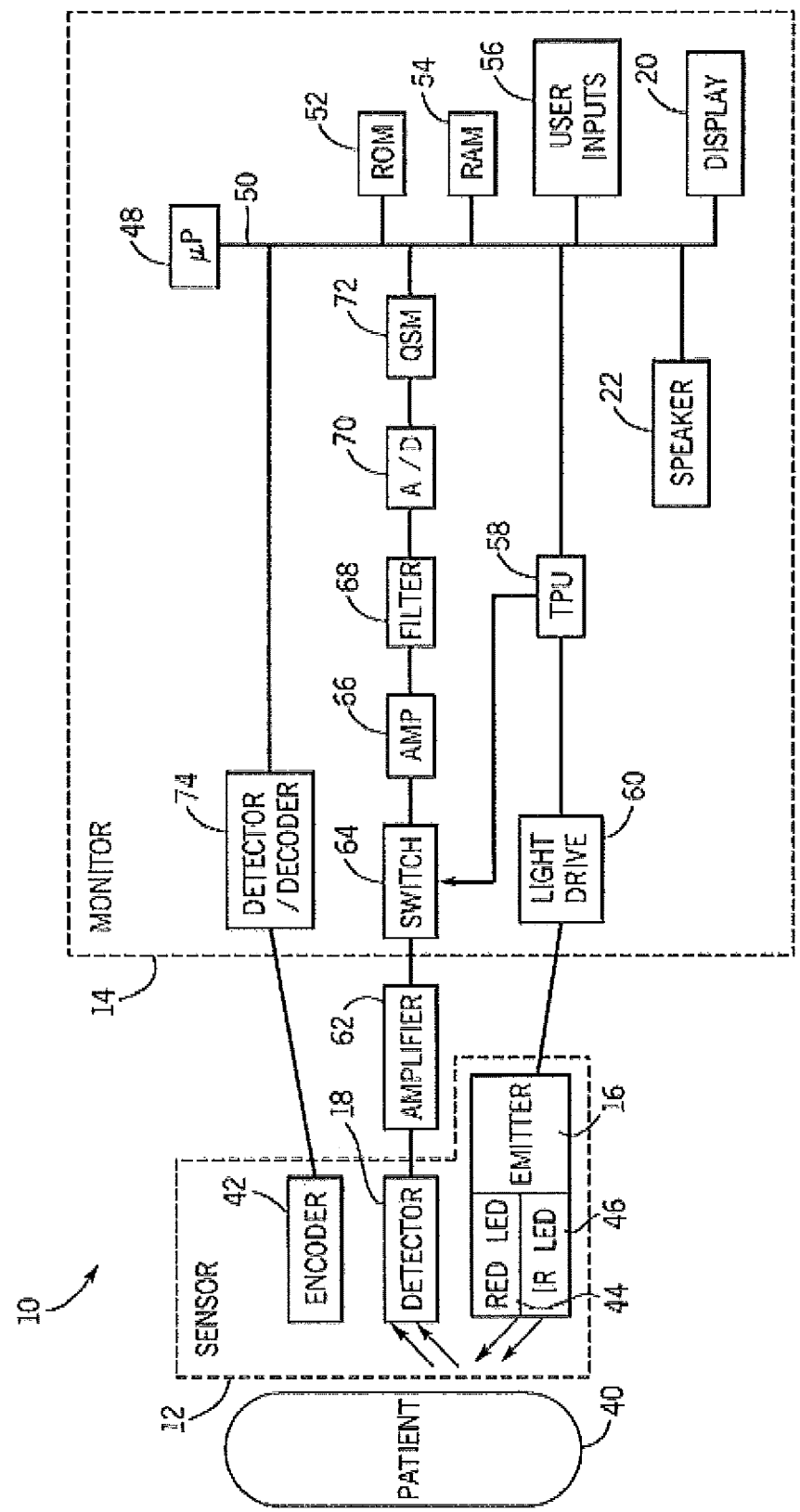
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40. For example, in an embodiment, the physiological parameters may be calculated using process 450 described below with reference to FIGS. 4a and 4b, and implemented on system 480 (described below with reference to FIG. 4c).

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

Signals corresponding to information about patient 40, and particularly about the intensity of light emanating from a patient's tissue over time, may be transmitted from encoder 42 to a decoder 74. These signals may include, for example, encoded information relating to patient characteristics, Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

In an embodiment, microprocessor 48 may determine the patient's physiological parameters, such as $SpO_2$ and pulse rate, using various algorithms and/or look-up tables based on the value of the received signals and/or data corresponding to the light received by detector 18.

Figure 3:
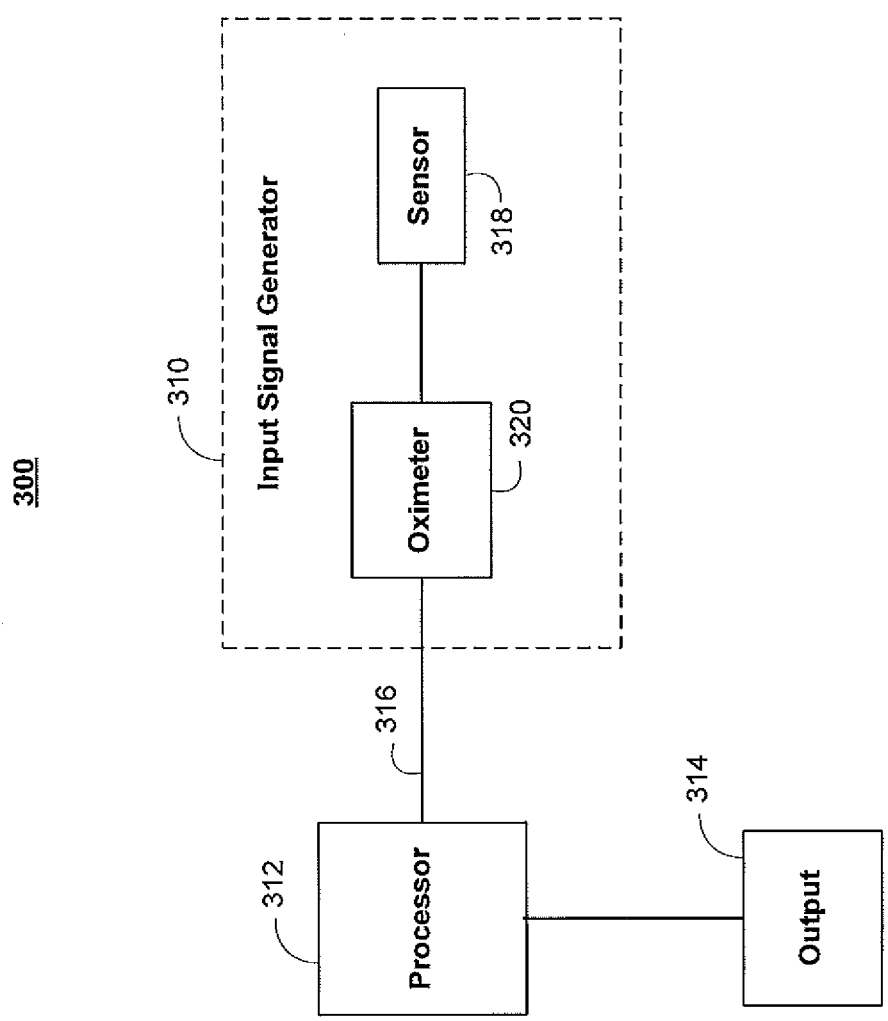
FIG. 3 is a block diagram of an illustrative signal processing system in accordance with an embodiment.

FIG. 3 is an illustrative signal processing system in accordance with an embodiment. In this embodiment, input signal generator 310 generates an input signal 316. As illustrated, input signal generator 310 may include oximeter 320 coupled to sensor 318, which may provide as input signal 316. In an embodiment, input signal 316 may be a PPG signal. It will be understood that input signal generator 310 may include any suitable signal source, signal generating data, signal generating equipment, or any combination thereof to produce signal 316. Signal 316 may be any suitable signal or signals, such as, for example, electrocardiogram, electroencephalogram, electrogastrogram, electromyograin, heart rate signals, pathological sounds, ultrasound, or any other suitable biosignal.

In this embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform calculations associated with the signals detected by detector 18 (FIG. 2). In an embodiment, processor 312 may perform the illustrative calculations described in process 450 (FIG. 4*b*) below to derive a measured value for a physiological parameter from the detected signals. Processor 312 may perform any suitable signal processing of signal 316 to filter signal 316, such as any suitable band-pass filtering, adaptive filtering, closed-loop filtering, and/or any other suitable filtering, and/or any combination thereof.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor 12 and monitor 14 and processor 312 may be implemented as part of monitor 14.

Figure 4A:
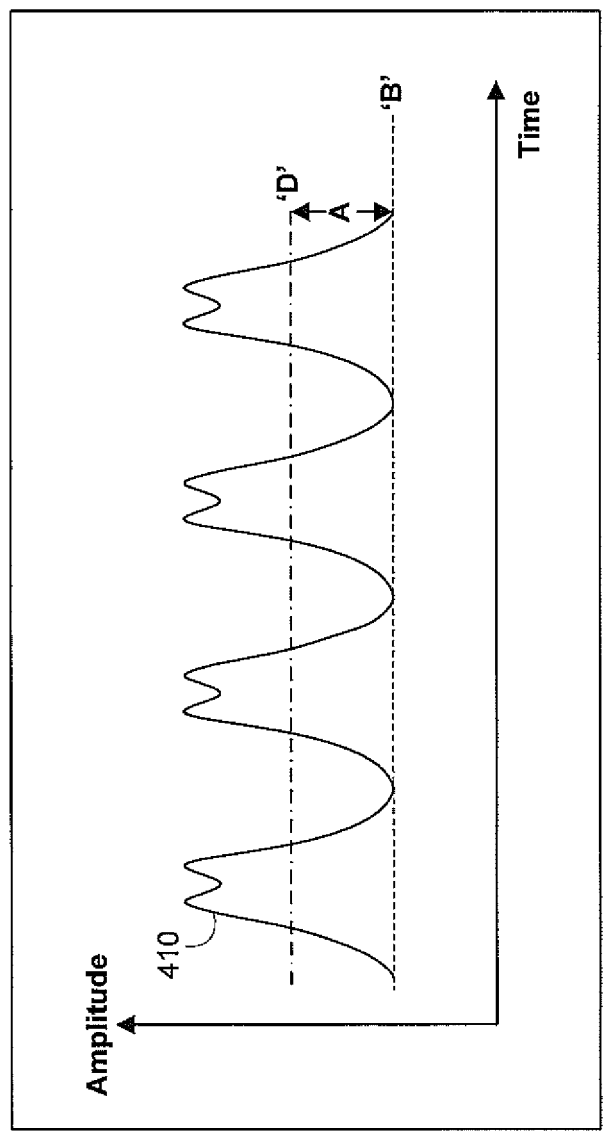
FIG. 4a is an illustrative waveform that may be used to determine physiological parameters in accordance with an embodiment.
Figure 4B:
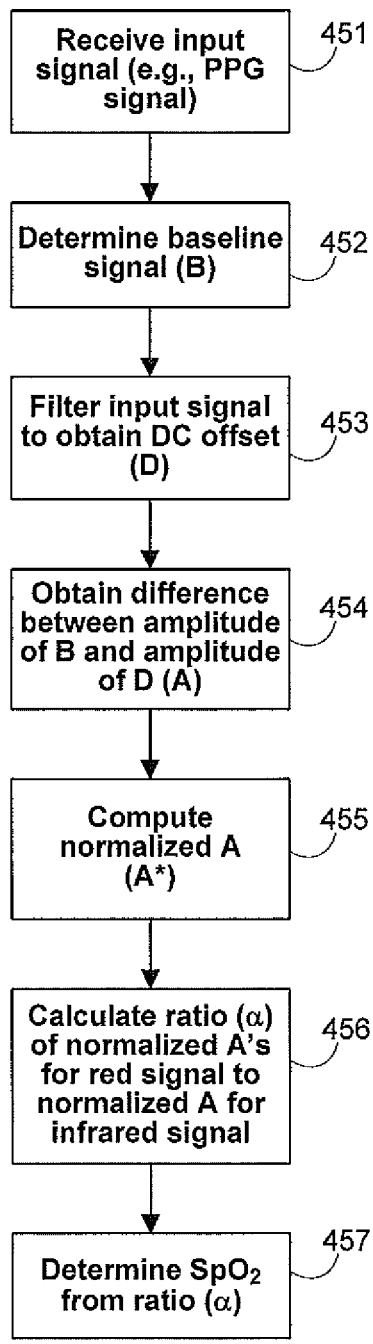
FIG. 4b is an illustrative flowchart of the operation of a signal processing system that may be used to determine physiological parameters in accordance with an embodiment.

The operation of an illustrative process 450 for determining the value of physiological parameters, such as $SpO_2$, will now be described with reference to FIGS. 4*a* and 4*b*. FIG. 4*a* is an illustrative waveform that may be used to determine physiological parameters in accordance with some embodiments. FIG. 4*b* is an illustrative flowchart of a process that may be used to determine physiological parameters in accordance with some embodiments. A photoplethysmographic signal 410 is received at step 451. For simplicity and clarity, it will be assumed that signal 410 is indicative of the blood oxygen saturation of a patient, although the disclosure is not limited as such. For example, signal 410 may be an illustrative time-varying signal that corresponds to the intensity of light transmitted from the red light source 44 (FIG. 2).

A baseline B for signal 410 may be determined at step 452. In an embodiment, the baseline B may be determined, at least in part, by finding a curve which passes through the bottom of the pulses. For example, the baseline B may be determined, at least in part, by a best-fit line through the trough points of signal 410, by curve-fitting (e.g., spline fit) which uses the trough points as reference, or by any other suitable algorithm. In an embodiment, the baseline B for each signal may be determined relative to a DC component of the signal (see below). In an embodiment, the baseline signal B may be determined based on the peaks of pulses.

The process continues to step 453 where signal 410 may be filtered to obtain a direct-current (DC) component D. The DC component D may be obtained using, for example, a low-pass filter having a frequency set below that of signal 410. Steps 452 and 453 may be reversed, performed simultaneously or concurrently, or in any suitable order.

At step 454, a difference A between the DC component D from step 453 and the baseline B from step 452 may be obtained. In an embodiment, two different kinds of filtering may be used to obtain the difference signal A. In such an embodiment, difference signal A may be obtained, at least in part, using the output of a first filter (e.g., a low-pass filter to obtain the DC component D) and the output of a second filter. The process continues at step 455 where the difference signal A is normalized to obtain normalized signal A*. In an embodiment, difference signal A may be normalized by dividing by DC component D. Other suitable normalizations may be used. For example, difference signal A may be normalized by dividing by the baseline signal B. Steps 451 to 455 is performed for both the Red and the Infrared light components of the physiological signal to obtain $A^*_R$ and $A^*_{IR}$, where $A^*_R$ is the normalized difference signal for the Red light and $A^*_{IR}$ is the normalized difference signal for the Infrared light. The process continues at step 456 where a ratio α for the normalized difference signals may be determined. In an embodiment, the ratio α may be determined as $$\alpha = \frac{A^*_R}{A^*_{IR}}.$$

At step 457, the ratio α may be used to determine the physiological parameters of the subject tinder examination. In an embodiment, the ratio α may be used by the microprocessor 48 (FIG. 2) to determine the patient's physiological parameters, such as $SpO_2$ and pulse rate, using various algorithms and/or look-up tables. For example, in an embodiment that determines $SpO_2$ based on entries in a lookup table, the ratio α may be used to determine a location in the lookup table. If no motion artifact is present, the data entry in the location corresponding to α is representative of the subject's blood oxygen saturation. In practice, however, α or the data entry retrieved from the table may require additional preprocessing or post-processing in order to remove artifacts.

In practice, one or more steps shown in process 450 may be combined with other steps, performed in any suitable order, performed in parallel (e.g., simultaneously or substantially simultaneously) or removed. An advantage of the processing techniques disclosed herein is that a value for the physiological parameter may be obtained without using the pulse information included in the PPG signal, thus requiring fewer computations that improve the accuracy and rate of obtaining data, compared to known techniques. A method or system of measuring physiological parameters based on the afore-mentioned embodiments may advantageously minimize reliance on the pulsatile part of the waveform. Therefore, erroneous information within the waveform, or certain changes in the structure of the pulse wave (e.g., the position of the dichrotic notch) have minimal if any adverse impact on the predictive value of the physiological parameter.

Figure 4C:
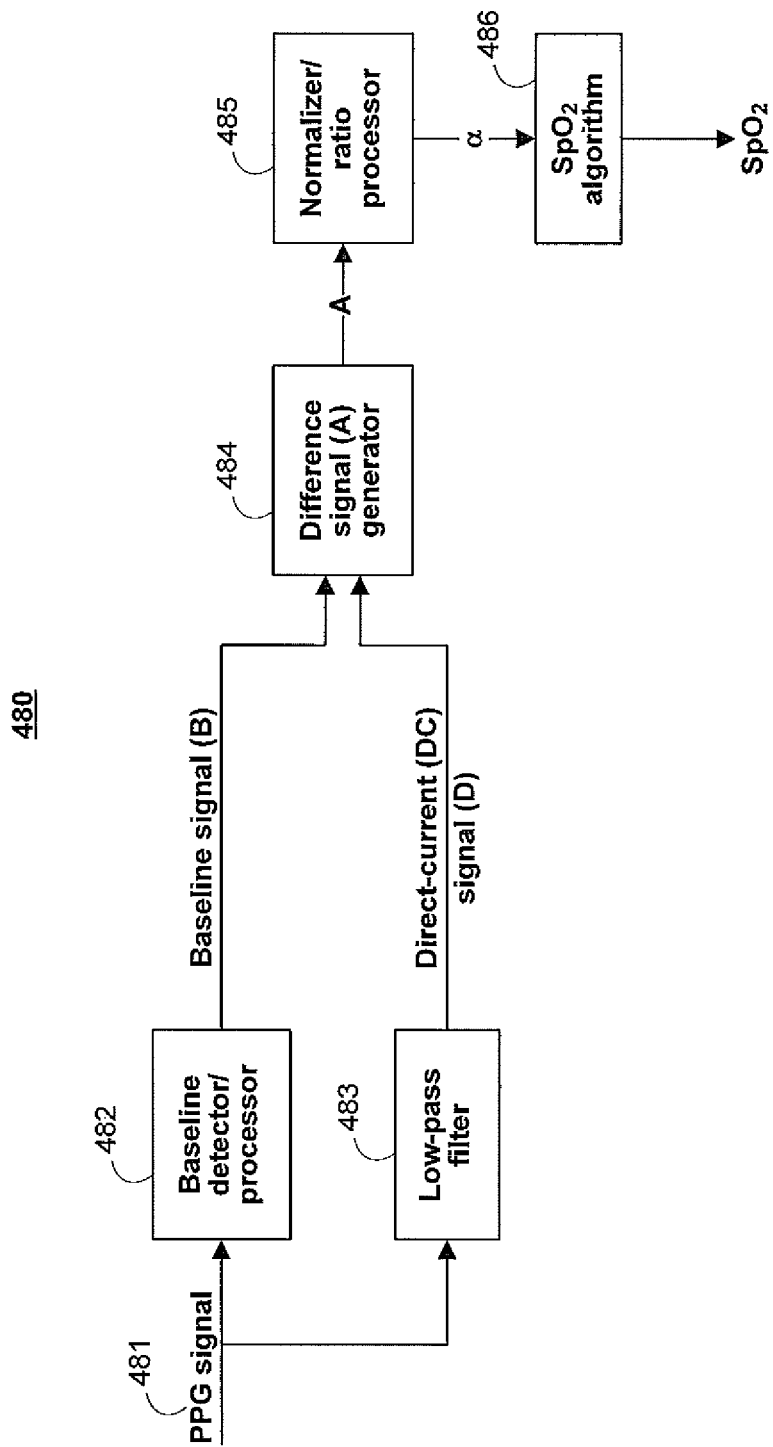
FIG. 4c is a block diagram of an exemplary signal processing system that may be used to determine physiological parameters in accordance with some embodiments.

FIG. 4c shows an exemplary signal processing system 480 that may be used by microprocessor 48 (FIG. 2) and/or processor 312 (FIG. 3) to implement illustrative process 450 (FIG. 4b) according to an embodiment. Baseline detector/processor 482 receives PPG signal 481, which is representative of a measured light intensity of light detected by detector 18 (FIG. 2). Baseline detector/processor 482 determines a baseline signal B for signal 481. In an embodiment, the baseline B may be determined based, at least in part, on a best-fit line through the troughs of pulses carried in signal 481. Other suitable methods, such as, curve-fitting (e.g., spline fit) which uses the troughs as references may be used. In an embodiment, the baseline B may be determined, at least in part, based on the peaks of the pulses carried in the PPG signal. Detector/processor 482 may determine an analysis window (i.e., the unit size of signals processed at a time) based on a fixed system parameter or in response to user input. In an embodiment, the analysis window may be dynamic, changing as signal conditions change. Baseline detector/processor 482 may be implemented using any suitable combination of hardware and/or software. Low-pass filter 483 also receives signal 481. Low-pass filter 483 filters the signal 481 at a frequency set to below that of signal 481 to at least substantially remove all pulse information. The output of low-pass filter 483 may be characterized as a direct-current (DC) component D of signal 481. DC component D and baseline signal B may be provided to difference signal generator 484 which generates a difference signal A, which represents the difference between baseline signal B and DC component D. Difference signal A may be provided to normalizer/ratio processor 485. Normalizer 485 normalizes the difference signal A for each of the Red light component and the Infrared light component of the PPG signal to obtain 481 normalize difference signals $A^*_R$ and $A^*_{IR}$, respectively. Normalizer 485 may normalize the difference signals using any suitable normalization. In an embodiment, normalizer 485 may normalize the difference signals by dividing by the respective baseline signal B. In some embodiments, normalizer 485 may normalize the difference signals by dividing by the respective DC component signal D. Ratio processor 485 computes a ratio α which represents the ratio of the normalized difference signal for the Red light $A^*_R$ to the normalized difference signal for the Infrared light $A^*_{IR}$. The ratio α is provided to $SpO_2$ algorithm processor 486, which generates a measured value for the patient's blood oxygen saturation based on the ratio. The ratio α may be used by $SpO_2$ algorithm processor 486 to determine the physiological parameters of the subject under examination. In an embodiment, the ratio α may be used by $SpO_2$ algorithm processor 486 to determine the patient's physiological parameters, such as $SpO_2$ and pulse rate, using various algorithms and/or look-up tables. Algorithms and look-up tables used to determine the $SpO_2$ may be based on empirical data.

It is understood that the components of system 480 are shown as separate for clarity and simplicity, and that any number of the components may be combined without departing from the scope of the disclosure.

The embodiments described herein may relate to determining one or more statistical parameters of data from which an estimated physiological parameter value has been determined. Statistical parameters associated with the physiological parameter may include parameters related to the accuracy of the estimated value such as error estimates and probability distributions of the data.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to electrocardiogram, electroencephalogram, electrogastrogram, electromyogram, heart rate signals, pathological sounds, ultrasound, or any other suitable biosignal.

The foregoing is merely illustrative of the principles of this disclosure and various modifications can be made by those skilled in the art without departing from the scope and spirit of the disclosure. The following claims may also describe various aspects of this disclosure.

What is claimed is:

1. A system for measuring a value of a physiological parameter of a subject, the system comprising a computer processor configured to:
   determine a first baseline signal for a first received waveform, wherein the first baseline signal corresponds to peak or trough information of the first received waveform, and a second baseline signal for a second received waveform, wherein the second baseline signal corresponds to peak or trough information of the second received waveform, the first and second received waveforms being indicative of the physiological parameter of the subject;
   filter the first and second received waveforms to obtain a first direct-current (DC) component for the first received waveform and a second DC component for the second received waveform;
   calculate a first difference signal $A_R$ for the first received waveform and a second difference signal $A_{IR}$ for the second received waveform, wherein the difference signal for each received waveform is based at least in part upon a difference between the DC component and baseline signal of the received waveform; and
   derive a measured value for the physiological parameter from the first and second difference signals.

2. The system of claim 1, wherein the processor is further configured to calculate a first normalized difference signal $A^*_R$ for the first received waveform and a second normalized difference signal $A^*_{IR}$ for the second received waveform, based on the difference signals $A_R$ and $A_{IR}$, respectively.

3. The system of claim 2, wherein the processor is configured to calculate a normalized difference signal for the received waveform by dividing the difference signal for the received waveform by the DC component of the received waveform.

4. The system of claim 2, wherein the processor is configured to calculate a normalized difference signal for the received waveform by dividing the difference signal for the received waveform by the baseline signal for the received waveform.

5. The system of claim 2, wherein the processor is configured to derive a measured value for the physiological parameter by deriving a measured value for the physiological parameter from a ratio of the first normalized difference signal $A^*_R$ with respective to the second normalized difference signal $A^*_{IR}$.

6. The system of claim 5, wherein the processor is configured to derive a measured value for the physiological parameter by deriving a measured value from a lookup table based on the ratio of the normalized difference signals.

7. The system of claim 1, wherein the processor is configured to determine a baseline signal for a received waveform by determining a best-fit line through the trough points of the received waveform.

8. The system of claim 1, wherein the physiological parameter is indicative of the blood oxygen saturation of the subject.

9. The system of claim 1, wherein the processor is further configured to generate an alarm if the measured value for the physiological parameter meets one or more predetermined conditions.

10. A system for measuring blood oxygen saturation of a subject, the system comprising a computer processor configured to:
    receive a first waveform (R) corresponding to a red light and a second waveform (IR) corresponding to an infrared light, the waveforms being indicative of the blood oxygen saturation of the subject;
    determine a first baseline signal $B_R$ for the first waveform, wherein the first baseline signal $B_R$ corresponds to peak or trough information of the first waveform, and a second baseline signal $B_{IR}$ for the second waveform, wherein the second baseline signal $B_{IR}$ corresponds to peak or trough information of the second waveform;
    filter the first and second waveforms to obtain a first direct-current (DC) component $D_R$ for the first waveform and second DC component $D_{IR}$ for the second waveform;
    obtain a first difference signal $A_R$ for the first waveform and a second difference signal $A_{IR}$ for the second waveform, wherein the difference signal for each of the first and second waveforms corresponds to a difference between the DC component and baseline signal of the waveform;
    calculate a first normalized difference signal $A^*_R$ for the first waveform and a second normalized difference signal $A^*_{IR}$ for the second waveform; and
    derive a measured value for the blood oxygen saturation from a ratio of the first normalized difference signal $A^*_R$ with respective to the second normalized difference signal $A^*_{IR}$.

11. Non-transitory computer-readable medium for use in measuring a value of a physiological parameter of a subject, the computer-readable medium having computer program instructions recorded thereon for:
    determining a first baseline signal for a first received waveform, wherein the first baseline signal corresponds to peak or trough information of the first received waveform, and a second baseline signal for a second received waveform, wherein the second baseline signal corresponds to peak or trough information of the second received waveform, the first and second received waveforms being indicative of the physiological parameter of the subject;
    filtering the first and second received waveforms to obtain a first direct-current (DC) component for the first received waveform and a second DC component for the second received waveform;
    calculating a first difference signal $A_R$ for the first received waveform and a second difference signal $A_{IR}$ for the second received waveform, wherein the difference signal for each received waveform is based at least in part upon a difference between the DC component and baseline signal of the received waveform; and deriving a measured value for the physiological parameter from the first and second difference signals.

12. Non-transitory computer-readable medium for use in measuring blood oxygen saturation of a subject, the computer-readable medium having computer program instructions recorded thereon for:

receiving a first waveform (R) corresponding to a red light and a second waveform (IR) corresponding to an infrared light, the waveforms being indicative of the blood oxygen saturation of the subject;

determining a first baseline signal $B_R$ for the first waveform, wherein the first baseline signal $B_R$ corresponds to peak or trough information of the first waveform, and a second baseline signal $B_{IR}$ for the second waveform, wherein the second baseline signal $B_{IR}$ corresponds to peak or trough information of the second waveform;

filtering the first and second waveforms to obtain a first direct-current (DC) component $D_R$ for the first waveform and second DC component $D_{IR}$ for the second waveform;

obtaining a first difference signal $A_R$ for the first waveform and a second difference signal $A_{IR}$ for the second waveform, wherein the difference signal for each of the first and second waveforms corresponds to a difference between the DC component and baseline signal of waveform;

calculating a first normalized difference signal $A^*_R$ for the first waveform and a second normalized difference signal $A^*_{IR}$ for the second waveform; and deriving a measured value for the blood oxygen saturation from a ratio of the first normalized difference signal $A^*_R$ with respective to the second normalized difference signal $A^*_{IR}$.

* * * * *